US006774382B2

(12) United States Patent
Yoshida

(10) Patent No.: US 6,774,382 B2
(45) Date of Patent: Aug. 10, 2004

(54) FLUORESCENT TRANSILLUMINATOR REQUIRING NO VISIBLE LIGHT-CUTTING FILTER

(75) Inventor: Hisashi Yoshida, Tokyo (JP)

(73) Assignee: NEC Corporation, Tokyo (JP)

( * ) Notice: Subject to any disclaimer, the term of this patent is extended or adjusted under 35 U.S.C. 154(b) by 29 days.

(21) Appl. No.: 10/318,187

(22) Filed: Dec. 13, 2002

(65) Prior Publication Data

US 2003/0116723 A1 Jun. 26, 2003

(30) Foreign Application Priority Data

Dec. 26, 2001 (JP) ........................................ 2001-395356

(51) Int. Cl.[7] ................................................ G01J 1/58
(52) U.S. Cl. ............................... 250/504 R; 250/458.1; 250/459.1
(58) Field of Search ......................... 250/504 R, 458.1, 250/459.1; 355/113, 114, 116, 118, 120

(56) References Cited

U.S. PATENT DOCUMENTS

| 5,327,195 | A | * | 7/1994 | Ehr ............................. 355/113 |
| 5,347,342 | A | * | 9/1994 | Ehr ............................. 355/113 |
| 5,449,446 | A | | 9/1995 | Verma et al. |
| 6,198,107 | B1 | * | 3/2001 | Seville ..................... 250/458.1 |
| 6,203,679 | B1 | * | 3/2001 | Bouis et al. ................. 204/466 |

FOREIGN PATENT DOCUMENTS

| EP | 1 067 166 | 1/2001 |
| JP | 2001-081460 | 3/2001 |
| JP | 2001-172624 | 6/2002 |

OTHER PUBLICATIONS

European Search report dated Sep. 16, 2003.
XP 002034301 article titled " Comparison of Various Ultraviolet Sources for Fluorescent Detection of Ethidium Bromide–DNA Complexes in Polyacrlamide Gels" vol. 82 dated 1977 pp. 455–462.
Abstract 02090425.6.

* cited by examiner

*Primary Examiner*—John R. Lee
*Assistant Examiner*—Erin-Michael Gill
(74) *Attorney, Agent, or Firm*—Whitham, Curtis & Christofferson, PC

(57) ABSTRACT

A fluorescent transilluminator according to the present invention comprises an ultraviolet source and a case housing the ultraviolet source. The ultraviolet source emits only ultraviolet rays of a sharp line spectrum. In the case, a transmission window, which passes ultraviolet rays toward an object to be irradiated, is formed as an opening thereof. In the transmission window, a visible light-cutting filter, which transmits ultraviolet rays and cuts visible light, is not installed. The ultraviolet source has particularly a fluorescent body, which is activated by gadolinium and emits ultraviolet rays, and an excitation source, which excites the fluorescent body through xenon discharge to make the fluorescent body fluoresce; and emits an emission of a spectrum having a peak emission wavelength at 313 nm with 5 nm or shorter half width.

10 Claims, 5 Drawing Sheets

FLUORESCENT TRANSILLUMINATOR REQUIRING NO VISIBLE LIGHT-CUTTING FILTER

BACKGROUND OF THE INVENTION

1. Field of the Invention

The present invention relates to a fluorescent transilluminator for exposing an object to be irradiated to ultraviolet rays to make it fluoresce.

2. Description of the Related Art

It has been known that a DNA analysis system uses gel electrophoresis as one of the remarkably effective techniques for analyzing nucleic acids or proteins. In the gel electrophoresis, an electric field is applied to a gel containing an electrolyte. Then, charged particles move in the gel. In this event, differences among the charged particles in size, shape, charge, and so on cause differences among respective moving rates of charged particles. Using the differences among the moving rates allows separating molecules of the nucleic acids, the proteins, or the like.

The nucleic acids separated by electrophoresis as described above are not visible, when they are left as they are, so, in order to observe the nucleic acid separated, the gel is stained with a solution of fluorescent substance (e.g., ethidium bromide) bindable to the nucleic acid. In some instances, a fluorescent substance such as ethidium bromide is previously added in preparing the gel. If the gel stained with fluorescent substance in this way is exposed to ultraviolet rays, portions corresponding to the nucleic acid fluoresce in orange. This allows observation of the nucleic acids. In this event, subjecting a marker, of which the molecular weight has been known, to electrophoresis together with a sample allows measurement of the molecular weight of the sample.

An ultraviolet lamp unit used for irradiating ultraviolet rays as described above is collectively named "fluorescent transilluminator".

In such an analysis, while the analysis is so far generally carried out on a photograph of fluorescing gel taken with a Polaroid camera, it is the recent method that the analysis is carried out with a computer on a series of images taken with a CCD camera, projected on a monitor, and recorded. In the latter case, since the analysis is carried out by measuring fluorescence strength, the recorded data is required to be precise.

For example, such a technique as described above is disclosed in Japanese Published Unexamined Patent Application No. 1993-215714, that the electrophoretically treated gel, of which internal molecule has been separated by gel electrophoresis, is mounted on an ultraviolet irradiation apparatus containing the ultraviolet lamp and is caused to fluoresce, and then the analysis of fluorescence is carried out using the computer. The ultraviolet irradiation apparatus disclosed in the publication has, as shown in FIG. 1, a structure in which a top surface of case 1 containing ultraviolet lamp 2 is covered with ultraviolet rays permeable glass 3. Electrophoretically treated gel 4 is exposed to ultraviolet rays, being mounted on the ultraviolet rays permeable glass 3.

A fluorescent transilluminator similar to this has been also disclosed in U.S. Pat. No. 5,347,342 and others. In the fluorescent transilluminator disclosed in the application, a top window (opening) is formed on the case containing an ultraviolet source. The top window has a structure in which a visible light-cutting filter (ultraviolet band filter) is installed and the sample is put above the visible light-cutting filter. Through this structure, ultraviolet rays emitted from the ultraviolet source are transmitted through the top window having the visible light-cutting filter and irradiated to the sample.

Generally, "ultraviolet rays (UV)" are the generic name of electromagnetic waves with wavelengths ranging from about 10 nm to 380 nm and is divided into the following 3 classes.

The first class comprises ultraviolet rays with wavelengths ranging from about 315 nm to 400 nm, which are called UV-A and also called near ultraviolet rays. These near ultraviolet rays have a pigmentation (so-called sunburn) function.

The second one comprises ultraviolet rays with wavelengths ranging from about 280 nm to 315 nm, which are called UV-B. The ultraviolet rays with these wavelengths cause erythema (irritating the skin). It is also said that this ultraviolet rays are necessary for biosynthesis of vitamin D.

The third one comprises ultraviolet rays with wavelengths ranging from 100 nm to 280 nm, which are called UV-C. This ultraviolet rays also called disinfecting rays have a literally disinfecting function.

For the fluorescent transilluminator, since ultraviolet rays in the UV-B band can effectively make a fluorescent substance (ethidium bromide) fluoresce, the light source that emits ultraviolet rays of the UV-B band is adopted. For the light source of such a fluorescent transilluminator as currently available in the market, a mercury fluorescent lamp, which is assembled with a fluorescent body such as ((Ca, Zn)$_3$(PO$_4$)$_2$:Tl) having an emission peak within a UV-B wavelength band ranging from about 280 to 315 nm, is used.

As described above, the light source of the fluorescent transilluminator used currently is a mercury-based light source lamp, in which mercury is sealed, such as an ultraviolet fluorescent lamp or a mercury lamp having a mercury line spectrum as its excitation source. In such a mercury-based light source lamp, when it is used in a low temperature atmosphere, the mercury vapor pressure reduces and the start of discharge becomes difficult. Moreover, after discharge is started, vapor pressure of sealed mercury rises in accordance with temperature increase after lighting of the lamp, emission strength thereby varies from immediately after the lamp is started until a condition becomes stable, and thus a long time is required to stabilize the light output. In this way, the mercury-based light source lamp conventionally used has a disadvantage of requiring a long start-up time particularly in cold districts and in the winter season. In addition, in the case where the mercury fluorescent lamp is used for an analysis of nucleic acids and proteins such as the abovementioned, because of the long required time to stabilize the light output and start the analysis, the problem may arise that before start of the analysis, a sample, particularly a delicate sample such as a DNA sample, is damaged.

Moreover, light emitted from the conventional mercury fluorescent lamp contains visible light components and hence, in the case where such a mercury fluorescent lamp is used as the light source, in order to assure that the visible light components do not adversely affect an observation, it becomes essential to use the visible light-cutting filter for transmitting ultraviolet rays and cutting the visible light. However, this filter is a peculiar filter and very expensive due to its specialty so that it costs 30 to 80 percent of the commercial price of a fluorescent transilluminator product.

Further, the mercury fluorescent lamp as the conventional light source of the fluorescent transilluminator provides such a weak emission strength that it may not make the sample for observation fluoresce sufficiently.

Therefore, it is an object of the present invention to provide a fluorescent transilluminator requiring no visible light-cutting filter. In addition, it is another object of the present invention to provide the fluorescent transilluminator, which is excellent in the start-up characteristic even in a low temperature atmosphere and can emit ultraviolet rays of strong intensity for making a sample fluoresce sufficiently.

SUMMARY OF THE INVENTION

With a purpose to achieve the above described objects, the fluorescent transilluminator according to the present invention has a light source emitting only ultraviolet rays with a sharp emission spectrum, particularly, the emission spectrum having a peak emission wavelength at 313 nm with 5 nm or shorter half width. Therefore, the fluorescent transilluminator according to the present invention can be adapted to irradiate an object with ultraviolet rays emitted by the ultraviolet source without cutting of visible light but only through a space and/or a member transmitting light having wave lengths equal to or longer than 300 nm, ranging from the ultraviolet region to the visible light region and this allows the transilluminator to assure that no disturbance occurs in the observation such as in gel electrophoresis. Consequently, a costly visible light-cutting filter is no longer required.

The ultraviolet source, which can emit such a sharp emission spectrum, can be formed by using a gadolinium-activated fluorescent body. Wherein, for an excitation source for exciting the fluorescent body to make it fluoresce, using xenon discharge is advantageously used. Utilization of such an excitation source using xenon discharge allows the ultraviolet source to be of an excellent start-up characteristic almost suffering no influence of an ambient temperature in contrast to the conventional mercury fluorescent lamp. Moreover, the ultraviolet source can emit an emission of stronger intensity than that of the conventional mercury fluorescent lamp.

In the fluorescent transilluminator according to the present invention, a transmission window formed of a glass plate can be installed, which can transmit light with wavelengths equal to or longer than 300 nm, ranging from the ultraviolet region to the visible light region, instead of that formed of a visible light-cutting filter in prior art. Installing such a transmission window allows mounting an object to be irradiated above this transmission window to irradiate advantageously the object.

The ultraviolet source can be, particularly, formed in a flat plate. Through this constitution, ultraviolet rays are emitted from one surface of the ultraviolet source and so it is easy to prevent exposure of an unnecessary site to ultraviolet rays. Moreover, forming a portion of the outer surface of the fluorescent transilluminator with a member constructing an emission surface of the ultraviolet source allows arranging the object to be irradiated directly on the member to raise irradiation efficiency of the object.

The above and other objects, features, and advantages of the present invention will become apparent from the following description with reference to the accompanying drawings, which illustrate examples of the present invention.

BRIEF DESCRIPTION OF THE DRAWINGS

FIG. 2b is a vertical sectional view along A—A line of FIG. 2a;

FIG. 3a is the sectional view showing an ultraviolet source of the fluorescent transilluminator of FIG. 2a;

FIG. 3b is a plan view showing an electrode pattern of the ultraviolet source of FIG. 3a;

DESCRIPTION OF THE PREFERRED EMBODIMENTS

An embodiment of a fluorescent transilluminator according to the present invention will be described in detail below with reference to the drawings.

Figure 1:
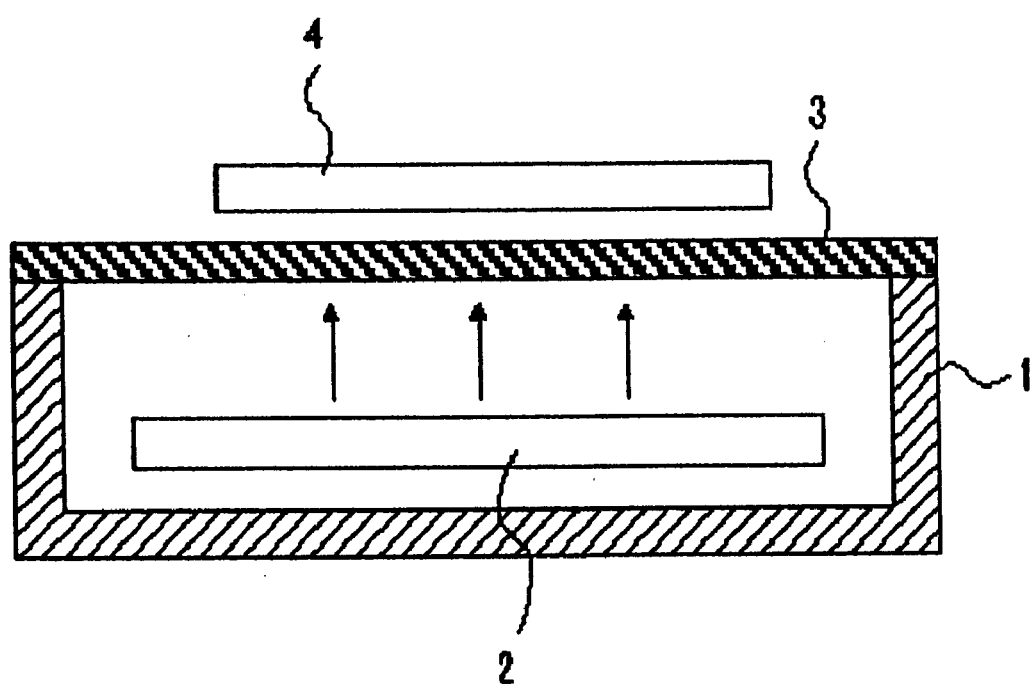
FIG. 1 is a sectional view showing a conventional fluorescent transilluminator.
Figure 2A:
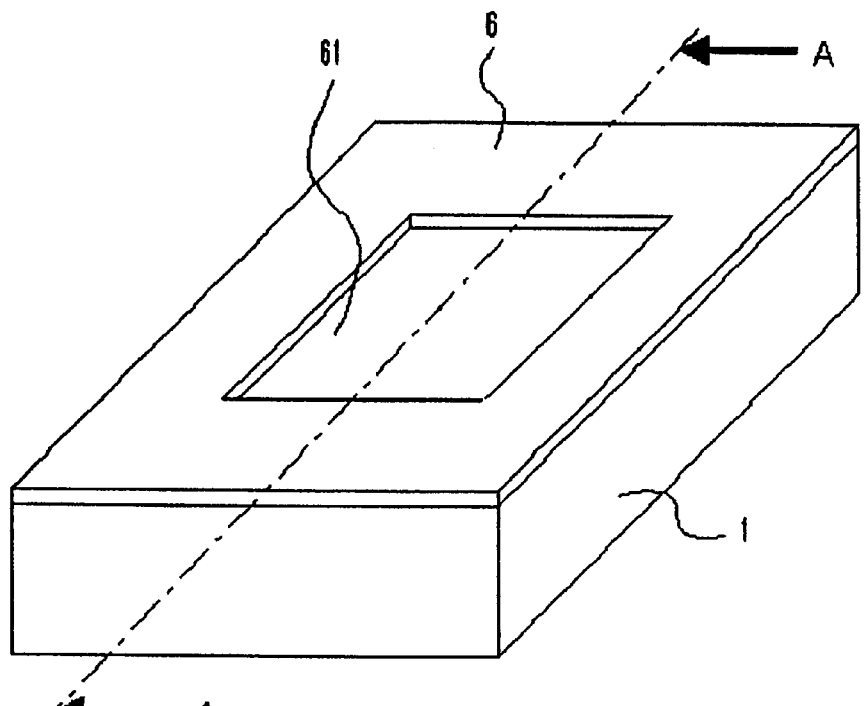
FIG. 2a is an external perspective view of a fluorescent transilluminator according to an embodiment of the present invention.
Figure 2B:
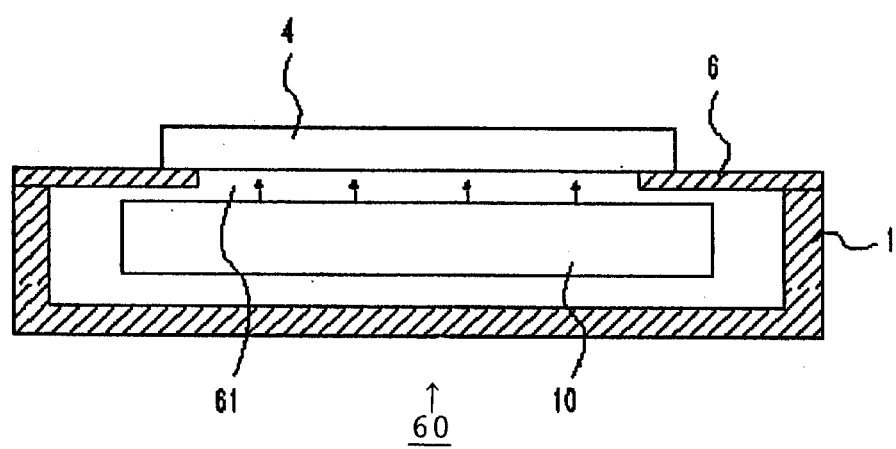

As show in FIG. 2a and FIG. 2b, fluorescent transilluminator 60 of the present embodiment has plate-like ultraviolet source 10 and case 1 housing it. Transmission window 61 is formed as an opening in top plate 6 of case 1. In a conventional fluorescent transilluminator, an ultraviolet transmission filter (a visible light-cutting filter) should be installed in the portion corresponding to transmission window 61. On the contrary, fluorescent transilluminator 60 of the present embodiment has, as illustrated herein, a novel constitution in which there is only the opening as transmission window 61 and no expensive filter is required. As described later, such a constitution becomes possible by using fluorescent transilluminator 60 that emits only ultraviolet rays with a sharp emission spectrum.

Fluorescent transilluminator 60 can be preferably applied for an analysis using gel electrophoresis. At the analysis, electrophoretically treated gel 4 stained with fluorescent substance is mounted above transmission window 61 as an object to be irradiated. In an example shown in FIG. 2b, the size of transmission window 61 is made smaller than that of electrophoretically treated gel 4 and electrophoretically treated gel 4 is mounted on an edge of transmission window 61. Ultraviolet rays emitted from ultraviolet source 10 pass through transmission window 61 to irradiate electrophoretically treated gel 4. Yet, in FIG. 2a, illustration of electrophoretically treated gel 4 is omitted.

The size of transmission window 61 can be larger than that of electrophoretically treated gel 4 and even in this case, electrophoretically treated gel 4 can be arranged above transmission window 61 through improving a method for mounting electrophoretically treated gel 4.

For example, it is a possible constitution that the top surface plate of plate-like ultraviolet source 10 is in close contact with the bottom surface of the edge of transmission window 61; in this case, a sample such as electrophoretically treated gel 4 having a smaller size than that of transmission window 61 can be directly mounted on the top face plate of ultraviolet source 10. Alternatively, it is also possible that the size of transmission window 61 coincides with that of the top face plate of ultraviolet source 10 and the top surface of top plate 6 lies with that of the top face plate of ultraviolet source 10 in a common plane. The constitutions in these ways, in which the top face plate of ultraviolet source 10 forms a portion of the outer surface of fluorescent transilluminator 60, have an advantage of possible efficient use of emitted ultraviolet rays.

On the other hand, a plate member such as a quartz glass plate transmitting light with wavelengths ranging from the ultraviolet band to visible light band, in other words, wavelengths of 300 nm or longer may be installed in transmission window 61. In comparison with the peculiar filter required in prior art, which transmits ultraviolet rays and cuts out visible light, such a plate member can be fabricated at a low cost; and thus the advantage of the present invention that a low fabrication cost is realized, is not lost even if this plate member is used.

Moreover, in the present embodiment, as described later, since the light source emitting only ultraviolet rays with the sharp emission spectrum having a peak emission wavelength at 313 nm with 5 nm or shorter half width is used as the ultraviolet source, it becomes possible to adopt an optical glass plate such as a cheap borosilicate glass, which passes light with wavelengths equal to or longer than 300 nm, ranging from the ultraviolet region to the visible light region, as the plate member fitted in transmission window 61. Adopting borosilicate glass plate allows fabricating a fluorescent transilluminator of strong market competitiveness and a high commercial value due to its low price.

Figure 3A:
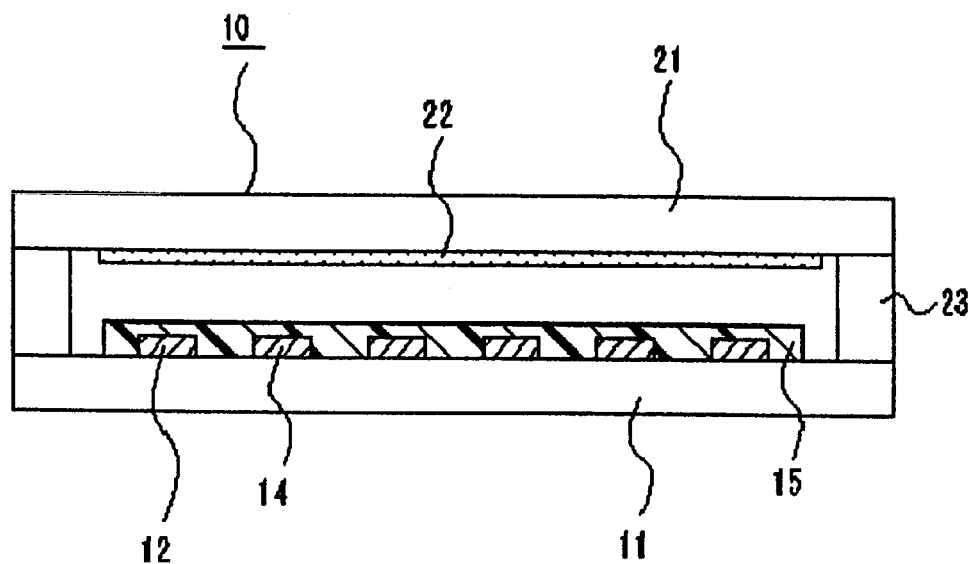
Figure 3B:
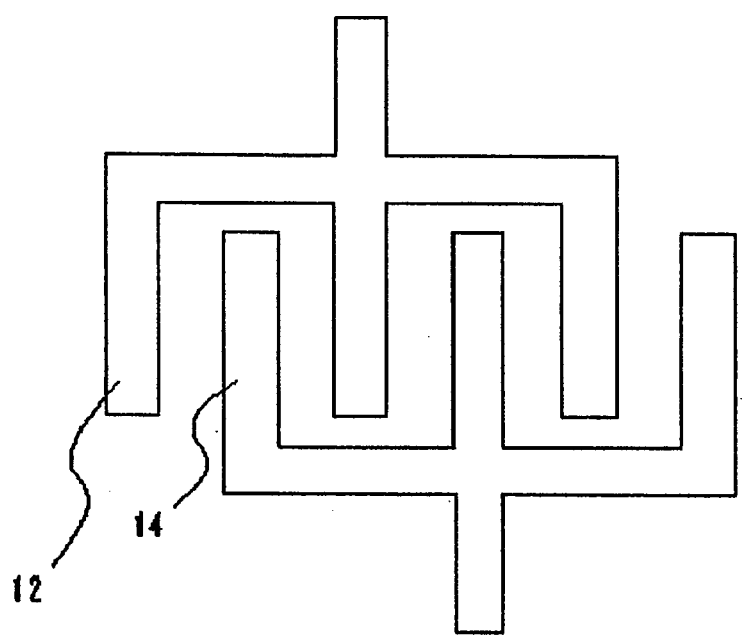

A constitution of plate-like ultraviolet source 10 according to the present embodiment will be described below with reference to FIG. 3a and FIG. 3b.

Ultraviolet source 10 has electrode substrate 11 consisting of a plate-like soda glass. On electrode substrate 11, as shown in FIG. 3b, finger-like electrode patterns 12 and 14 are formed through applying a conductive paste consisting of silver or copper, for example, used as an electrode material by screen-printing method.

On electrode patterns 12 and 14, dielectric material layer 15 is formed, which is comprised of a dielectric material mainly consisting of silica, wherein, on the uppermost layer of dielectric material layer 15, a layer consisting of a secondary electron-emitting material such as magnesium oxide, which also serves as a protecting film, and/or an ultraviolet-emitting fluorescent body may be formed.

On the other hand, opposite substrate 21 is arranged facing to the surface of electrode substrate 11 on the side of electrode patterns 12 and 14. The rays are emitted in the direction toward opposite substrate 21. As opposite substrate 21, an ultraviolet rays permeable glass such as an optical glass can be used and ultraviolet fluorescent body layer 22 ranging from 20 to 50 $\mu$m in thickness is printed on the surface thereof facing to electrode substrate 11.

Between electrode substrate 11 and opposite substrate 21, glass frame 23 is installed as a spacer for locating these two members in parallel to each other to secure a prescribed discharge space. Glass frame 23 is attached to electrode substrate 11 and opposite substrate 21 by fusion bonding. In this way, the inside of the discharge space surrounded by these members is hermetically sealed. As the spacer between electrode substrate 11 and the opposite substrate 21, a member other than the glass frame may be used if it can hermetically seal the space.

The discharge space formed in this way is evacuated and instead a rare gas is sealed in the discharge space. As the rare gas to be sealed, a xenon (Xe) gas, a mixture gas consisting of Xe and argon (AR), or a mixture gas consisting of Xe, Ar, and neon (Ne) can be used.

Ultraviolet source 10 can emit through application of a sinusoid wave or a pulse wave of several 10 kHz frequencies between electrode patterns 12 and 14. In other words, application of a voltage between electrode patterns 12 and 14 causes the xenon gas to discharge and emit vacuum ultraviolet radiation. This vacuum ultraviolet radiation is absorbed by fluorescent body layer 22 and then, fluorescent body layer 22 emits ultraviolet rays.

For ultraviolet source 10, a fluorescent body activated by gadolinium (Gd) is used to form ultraviolet fluorescent body layer 22 instead of the ultraviolet fluorescent body such as $(Ca, Zn)_3(PO_4)_2$:Tl which has been conventionally used. As the ultraviolet fluorescent body activated by gadolinium used for the present embodiment, particularly, an $YB_xO_y$:Gd fluorescent body (x and y are arbitrary positive integer) such as $YBO_3$:Gd fluorescent body is preferably used. Preferable examples of various specific compositions will be described later.

When such a fluorescent body is adopted, an emission with a sharp line spectrum can be generated in contrast with a conventional thalium (Tl)-activated fluorescent body. The emission wavelengths of ultraviolet source 10 are in the UV-B band ranging from 280 nm to 315 nm. The present inventor found that, by the use of ultraviolet source 10 irradiating ultraviolet rays of such a sharp line spectrum, not only effective fluorescent luminescence of a pigment for light emission of a DNA, e.g., ethidium bromide, but also observation of the necessary fluorescence only from the DNA, the other extra light being nearly excluded, could be realized.

Figure 4:
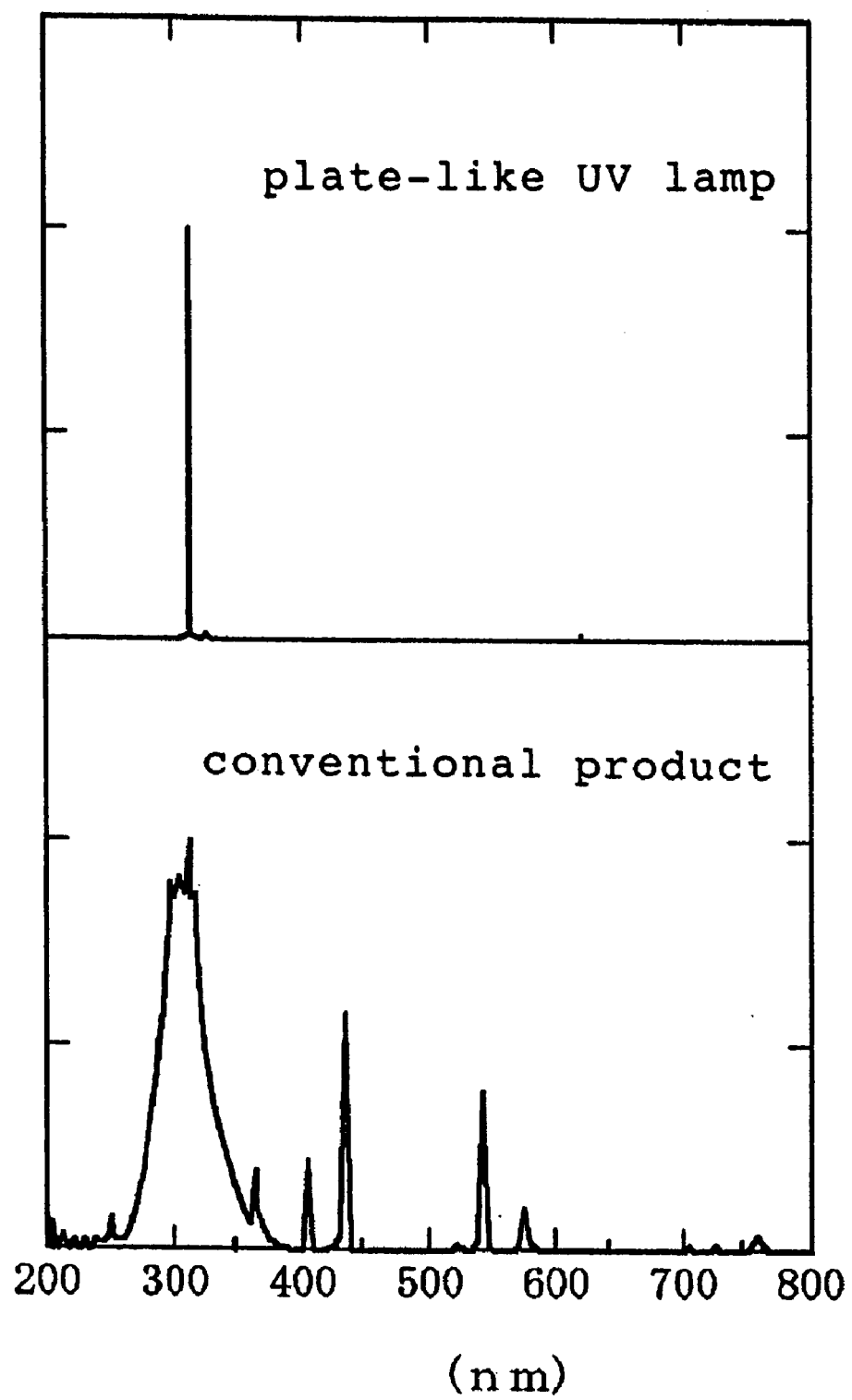
FIG. 4 is a graph showing emission spectra of the fluorescent transilluminator of FIG. 2a and a conventional one.

The difference between the emission spectrum of an existing mercury fluorescent lamp and that of ultraviolet source 10 of the present embodiment will be described below with reference to FIG. 4. In a conventional product, emission is observed not only in the ultraviolet region but also in the visible light region. In contrast, in ultraviolet source 10 adopted in the present embodiment, the sharp emission spectrum having a peak emission wavelength at 313 nm with 5 nm or shorter half width is generated and no emission is present in the visible light region. Therefore, cutting of visible light disturbing the observation is not required for ultraviolet source 10 as required in the case where the conventional mercury fluorescent lamp is used. Consequently, according to the present embodiment, the fluorescent transilluminator 60, which requires no expensive ultraviolet rays permeable filter and hence is low priced and has a high commercial value, can be realized.

In the case where $(Ca, Zn)_3(PO_4)_2$:Tl was used as the above described conventional ultraviolet fluorescent body, measurement of ultraviolet irradiation strength showed 8 mW/cm$^2$. On the other hand, use of the fluorescent body activated by Gd showed an increase in irradiation strength (lamp strength). Table 1 shows a detailed result.

TABLE 1

| No. | Composition | Emission strength | No. | Composition | Emission strength |
|---|---|---|---|---|---|
| 1 | YBO$_3$:Gd | 9.0 | 8 | LaP$_3$O$_9$:Gd | 8.4 |
| 2 | YB$_2$O$_5$:Gd | 9.5 | 9 | SrB$_4$O$_7$:Gd | 8.3 |

TABLE 1-continued

| No. | Composition | Emission strength | No. | Composition | Emission strength |
|---|---|---|---|---|---|
| 3 | NaGdSiO$_4$ | 8.3 | 10 | LaPO$_4$:Gd | 8.2 |
| 4 | YAl$_3$(BO$_3$)$_4$:Gd | 8.1 | 11 | LaMgB$_5$O$_{10}$:Gd, Pr | 9.7 |
| 5 | LaBO$_3$:Gd | 8.2 | 12 | LaB$_3$O$_8$:Gd, Pr | 9.8 |
| 6 | YPO$_4$:Gd | 8.6 | 13 | (Ca,Zn)$_3$(PO$_4$)$_2$:Tl (Conventional) | 8.0 |
| 7 | YAlO$_3$:Gd | 8.3 | | | |

From Table 1, it can be understood that use of preferable various ultraviolet emitting fluorescent body activated by Gd yields stronger fluorescence in comparison with the conventional ultraviolet fluorescent body. In this way, fluorescence can be emitted effectively from the sample.

Moreover, in the present embodiment, a light source containing no mercury is adopted as ultraviolet source 10. The difference between start-up states of the existing mercury fluorescent lamp and this ultraviolet source 10 will be described as follows with reference to FIG. 5.

Figure 5:
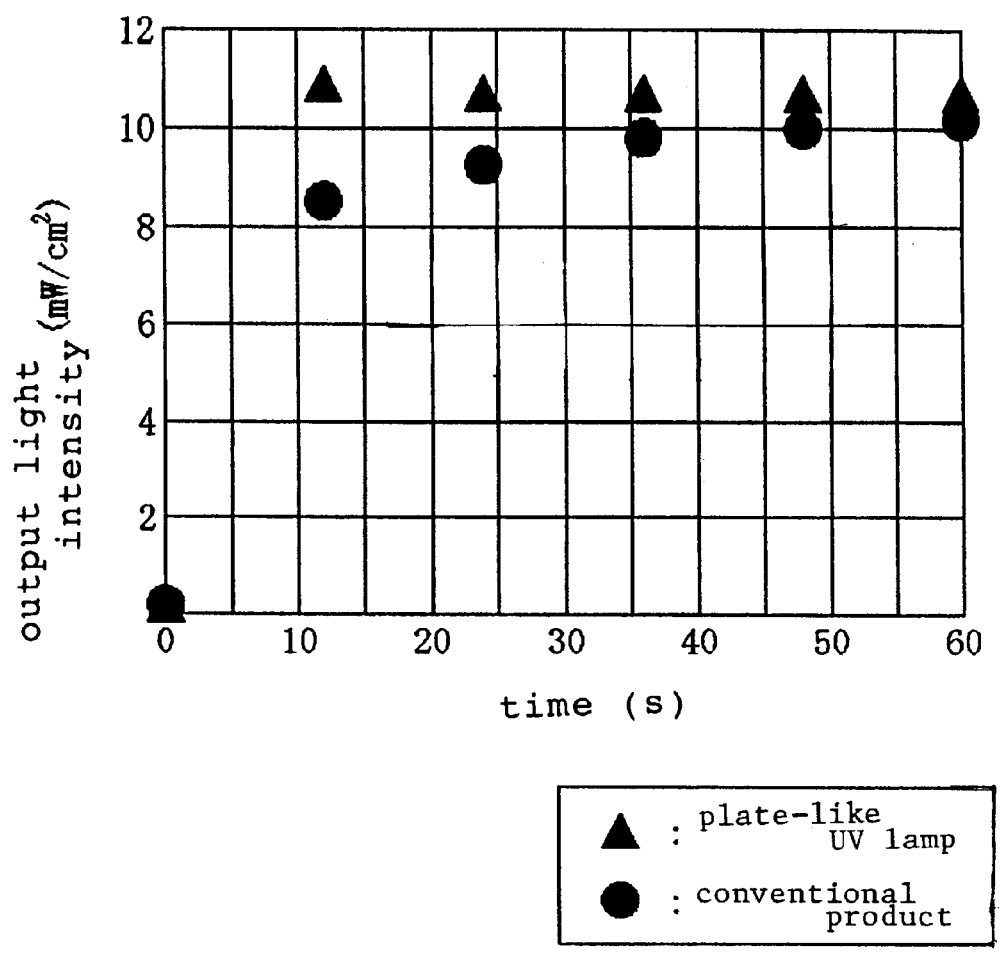
FIG. 5 is a graph showing a start-up characteristic of the fluorescent transilluminator of FIG. 2a and a conventional one.

FIG. 5 shows that time of about 50 seconds is required until the light output has become stable in the conventional mercury fluorescent lamp. In other words, at least 50 seconds is required for the mercury vapor in a tube to become stable. Thus, in case of using the conventional mercury fluorescent lamp, a problem may arise in that an adverse effect occurs in the sample, such as that the DNA as the object of observation is damaged before emission becomes stable. Moreover, the start-up characteristic of the conventional mercury fluorescent lamp tends to further deteriorate in a low temperature atmosphere.

On the other hand, ultraviolet source 10 used in fluorescent transilluminator 60 according to the present embodiment can reach the stable emission state rapidly compared with the conventional one, that is, immediately after it is turned on, it can yield a 100% light output. Hence, according to the present embodiment, damage of a sample such as the DNA before observation can be reduced. In addition, the start-up characteristic of ultraviolet source 10 in the present embodiment is not generally influenced by an atmospheric temperature and thus, ultraviolet source 10 is suitable particularly for use in cold districts and in winter season.

As described above, ultraviolet source 10 in the present embodiment has excellent characteristics, that is, emission of only ultraviolet rays with a sharp line spectrum, rapid start-up, almost no effect from the atmospheric temperature, and stronger emission than the conventional mercury fluorescent lamp are acquired. When such ultraviolet source 10 is used for fluorescent transilluminator 60, the following very useful effects are obtained: the visible light-cutting filter, which is expensive and necessary in prior art, becomes unnecessary and product cost is, therefore, reduced, the adverse effect on a delicate sample can be reduced, and the sample can be effectively fluoresced to present a good analysis.

An advantageous light source for use as the ultraviolet source of the fluorescent transilluminator in this way is not restricted to those as described above, but any one having a constitution, in which vacuum ultraviolet radiation generated by xenon discharge is absorbed by the fluorescent body activated by Gd to emit ultraviolet rays, may be used.

The ultraviolet source can be actuated by the sinusoidal wave and the pulse wave, namely, use of a DC inverter and, therefore, electrical power consumption can be saved. Moreover, since consumables such as a cathode and a filament are not used, the ultraviolet source has an advantage of having a long life.

The ultraviolet source may have the constitution, as described in the present embodiment, having the flat plate-like shape and emitting the light from one surface thereof. This constitution allows a reduction of the amount of ultraviolet rays incident on an unnecessary portion to result in the decreasing of deterioration of tools caused by ultraviolet rays. However, the ultraviolet source can be formed in a tube shape. In the latter case, a tubular member forming a discharge space is formed with a material such as glass passing UV-B ultraviolet rays.

While preferred embodiments of the present invention have been described using specific terms, such description is for illustrative purposes only, and it is to be understood that changes and variations may be made without departing from the spirit or scope of the following claims.

What is claimed is:

1. A fluorescent transilluminator housing an ultraviolet source and emitting ultraviolet rays from said ultraviolet source to an outside object to be irradiated, wherein
    said ultraviolet source emits only ultraviolet rays having a sharp line spectrum and the ultraviolet rays from said ultraviolet source is irradiated to said object through a space and/or a member transmitting light with wavelengths equal to or longer than 300 nm ranging from the ultraviolet region to the visible light region.

2. A fluorescent transilluminator according to claim 1, wherein said ultraviolet source emits an emission of the spectrum having a peak emission wavelength at 313 nm with 5 nm or shorter half width.

3. A fluorescent transilluminator according to claim 1, wherein said ultraviolet source has a fluorescent body emitting ultraviolet rays and an excitation source exciting said fluorescent body to make it fluoresce, said fluorescent body being activated by gadolinium.

4. A fluorescent transilluminator according to claim 1, wherein said ultraviolet source has a fluorescent body emitting ultraviolet rays and an excitation source exciting said fluorescent body to make it fluoresce, and said excitation source uses xenon discharge.

5. A fluorescent transilluminator according to claim 1, wherein a transmission window, which is formed of a glass plate transmitting light with wavelengths equal to or longer than 300 nm ranging from the ultraviolet region to the visible light region, is installed between said ultraviolet source and said object to be irradiated.

6. A fluorescent transilluminator according to claim 1, wherein said object to be irradiated is an electrophoretically treated gel stained with fluorescent substance.

7. A fluorescent transilluminator according to claim 1, wherein said ultraviolet source has a flat plate-like external shape.

8. A fluorescent transilluminator according to claim 7, wherein a member constructing an emission surface of said ultraviolet source forms a portion of an outer surface of said fluorescent transilluminator.

9. A fluorescent transilluminator, which irradiates an electrophoretically treated gel stained with fluorescent substance with ultraviolet rays having a wavelengths ranging from 280 to 315 nm, wherein a transmission window, which passes light of wavelengths equal to or longer than 300 nm ranging from the ultraviolet region to the visible light region, is installed between the ultraviolet source housed in the fluorescent transilluminator and said electrophoretically treated gel.

10. A fluorescent transilluminator housing an ultraviolet source and emitting ultraviolet rays from said ultraviolet source to an outside object to be irradiated, wherein said ultraviolet source has a fluorescent body which is activated by gadolinium and emits ultraviolet rays; an excitation source which excites said fluorescent body through xenon discharge to make said fluorescent body fluoresce; and a plate-like external shape, wherein a member constructing an emission surface of said ultraviolet source forms a portion of an outer surface of the fluorescent transilluminator.

* * * * *